United States Patent [19]

Packer et al.

[11] Patent Number: 5,402,796
[45] Date of Patent: Apr. 4, 1995

[54] ARTERIAL $CO_2$ MONITOR AND CLOSED LOOP CONTROLLER

[75] Inventors: John S. Packer, Camberwell; John F. Cade, Kew; Eng-Boon L. Law, Camberwell, all of Australia

[73] Assignee: University of Melbourne, Victoria, Australia

[21] Appl. No.: 30,123

[22] PCT Filed: Sep. 19, 1991

[86] PCT No.: PCT/A091/00435
  § 371 Date: Apr. 21, 1993
  § 102(e) Date: Apr. 21, 1993

[87] PCT Pub. No.: WO92/04865
  PCT Pub. Date: Apr. 2, 1992

[30] Foreign Application Priority Data

Sep. 19, 1990 [AU] Australia .................. PK2403

[51] Int. Cl.$^6$ .................................................. A61B 5/08
[52] U.S. Cl. ........................... 128/719; 128/200.24; 128/204; 128/22; 128/716; 73/23.3
[58] Field of Search ............. 128/716, 719, 200.24, 128/204.21-204.24; 73/23.3; 422/84

[56] References Cited

U.S. PATENT DOCUMENTS

| | | | |
|---|---|---|---|
| 3,927,670 | 12/1975 | Turney et al. | 128/719 |
| 4,368,740 | 1/1983 | Binder | 128/719 |
| 4,393,869 | 7/1983 | Boyarsky et al. | 128/204.21 X |
| 4,986,268 | 1/1991 | Tehrani | 128/204.22 |
| 5,107,831 | 4/1992 | Halpern et al. | 128/204.21 |
| 5,129,401 | 7/1992 | Corenman et al. | 128/719 |
| 5,320,093 | 12/1994 | Raemer | 128/204.23 X |

*Primary Examiner*—Lee S. Cohen
*Assistant Examiner*—Brian L. Casler
*Attorney, Agent, or Firm*—Fulwider Patton Lee & Utecht

[57] ABSTRACT

The arterial $CO_2$ monitor and closed loop controller for use with a ventilator monitors a patient's breath and determines $PaCO_2$ based upon a determination of a deadspace ratio, which is the ratio of the alveolar deadspace to alveolar tidal volume. The method generally comprises the steps of continuously monitoring measurable parameters of a patient's breath; obtaining an input value of $PaCO_2$ from a blood sample of the patient and using the patients breath parameters and the input value to calculate the deadspace ratio; and continuously determining $PaCO_2$ based on the assumption that the deadspace ratio subsequently remains constant. Decision rules obtained from other measurable data are preferably also used to identify the onset of changes in the deadspace ratio, and a new deadspace ratio is then determined from the patient's breath parameters and further input value of $PaCO_2$ from the patient's blood sample.

12 Claims, 5 Drawing Sheets

ARTERIAL CO2 MONITOR AND CLOSED LOOP CONTROLLER

BACKGROUND OF THE INVENTION

Field of the Invention

This invention related to a method and apparatus for continuously and non-invasively monitoring arterial blood $CO_2$ partial pressure ($PaCO_2$) of artificially ventilated patients.

DESCRIPTION OF RELATED ART

Mechanical ventilation is required by patients in an intensive care unit who are unable to control their own respiration. The rate of ventilation must be adjusted so that arterial $CO_2$ is within a desirable range. Conventionally clinicians adjust the ventilator settings based on periodically drawn blood samples. In order to monitor rapidly changing $PaCO_2$ (for monitoring or closed loop control purposes), a continuous and non-invasive monitor is desirable. Known transcutaneous transducers are non-invasive but require heating of the patient's skin to 44° C. and a long stabilization time of 30 minutes which renders them unsatisfactory for continuous monitoring. The known method of assuming a constant arterial to end-tidal $CO_2$ difference is not reliable during ventilation/perfusion changes, and attempts to implement closed loop ventilation control have failed largely due to the inability to continuously and non-invasively observe the variable to be controlled, that is, the $PaCO_2$.

Thus, the direct methods of monitoring $PaCO_2$ are invasive, and indirect methods are not reliable, particularly because end-tidal $CO_2$ is influenced by deadspace, which is an unmeasurable quality.

It would thus be desirable to provide a method and apparatus for providing a continuous and substantially non-invasive $PaCO_2$ estimation.

SUMMARY OF THE INVENTION

Briefly, and in general terms the invention provides a method and apparatus for continuously and non-invasively monitoring arterial blood $CO_2$ partial pressure ($PaCO_2$) of artificially ventilated patients, by monitoring a patient's breath and determining $PaCO_2$ based upon a determination of a deadspace ratio, which is the ratio of the alveolar deadspace to alveolar tidal volume. The method generally comprises the steps of continuously monitoring, measurable parameters of a patient's breath; obtaining an input value of $PaCO_2$ from a blood sample of the patient and using the patients breath parameters and the input value to calculate the deadspace ratio; and continuously determining $PaCO_2$ based on the assumption that the deadspace ratio subsequently remains constant.

Decision rules obtained from other measurable data are preferably also used to identify the onset of changes in the deadspace ratio, and a new deadspace ratio is then determined from the patient's breath parameters and a further input value of $PaCO_2$ from the patient's blood sample.

The determination of $PaCO_2$ is preferably based upon the equation $$\frac{V_D^{alv}}{V_T^{alv}} = \frac{PaCO_2 - P\bar{E}^*CO_2}{PaCO_2 - PiCO_2}$$

where $V_D^{alv}$ is the alveolar deadspace,
$V_T^{alv}$ is the alveolar tidal volume,
$P\bar{E}.CO_2$ is the mixed-expired $CO_2$ from the alveolar tidal volume, and
$PiCO_2$ is inspired $CO_2$.

The mixed-expired $CO_2$, inspired $CO_2$, alveolar tidal volume and the alveolar deadspace are the measurable parameters of the patient's breath.

The other measurable data used to determine decision rules for identifying changes in the deadspace ratio are preferably related to lung mechanics and trends in $CO_2$ production.

The method preferably further involves adjusting patient ventilation based on the determined value of $PaCO_2$.

In another aspect of the invention, an apparatus is provided for continuously and non-invasively monitoring arterial blood $CO_2$ partial pressure ($PaCO_2$) of artificially ventilated patients. The apparatus preferably includes a capnograph for monitoring continuously measurable parameters relevant to a patient's breath and providing data relating thereto, and means for determining a deadspace ratio connected to the capnograph to receive the breath parameter data and adapted to receive information relating to the $PaCO_2$ of a blood sample of the patient based upon the $PaCO_2$ information and the breath parameter data. Means are also preferably provided for continuously determining $PaCO_2$ based on the deadspace ratio, and the assumption that the deadspace ratio remains subsequently constant. However, means are also preferably provided for further receiving decision rules enabling identification of the onset of changes in the deadspace ratio to thereby signal the need for a further blood sample to re-calculate the deadspace ratio.

The apparatus is preferably connected to a mechanical ventilator to control operation of the ventilator based on the values of $PaCO_2$ determined by the apparatus.

These and other aspects and advantages of the invention will become apparent from the following detailed description, and the accompanying drawings, which illustrate by way of example the features of the invention.

DETAILED DESCRIPTION OF THE PREFERRED EMBODIMENTS

Figure 1:
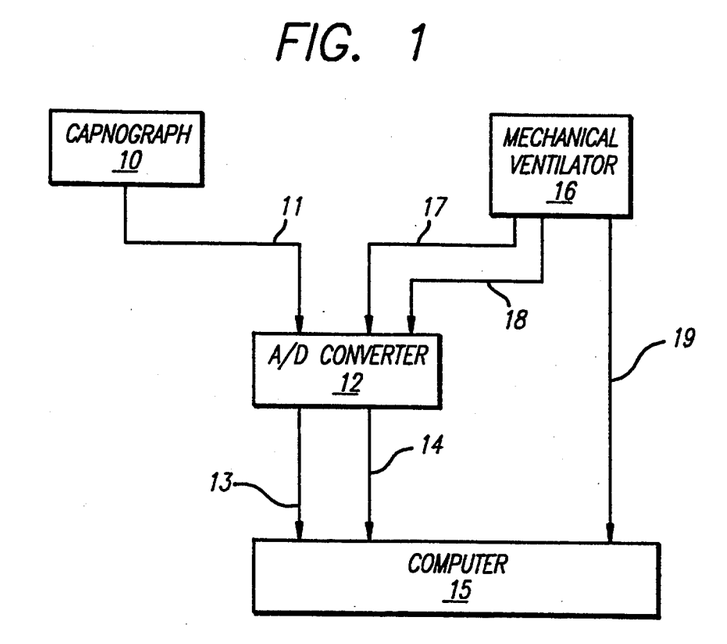
FIG. 1 is a basic functional block diagram of the apparatus of the invention.
Figure 2:
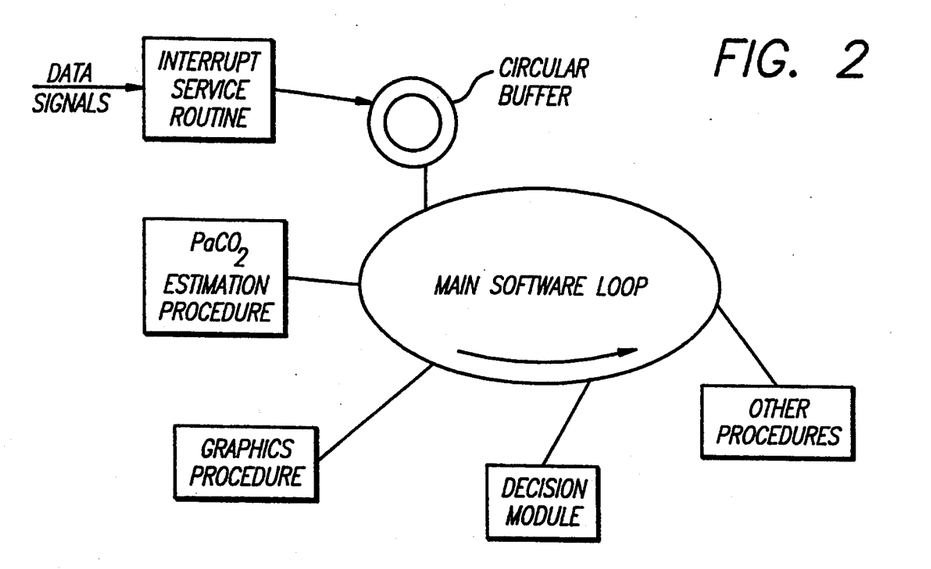
FIG. 2 is a block diagram in the form of a software flow chart for the apparatus of FIG. 1.

In FIG. 1 the outlet port of capnograph 10 is connected, via connection 11, to analogue to digital (A/D) converter 12. The capnograph 10 may, for example, be a HP-78356 and the A/D converter 12 may comprise analogue devices such as an RT1-815.

The A/D converter 12 is connected via connections 13 and 14 to computer 15 which may, for example, be an IBM compatible PC-AT286. The connection 13 is to the interrupt port of the computer 15 and the connection 14 is to the data port.

A mechanical ventilator 16 such as a Puritan-Bennett 7200 is typically connected both to the A/D converter 12 and the computer 15 as shown. The connections 17 and 18 are to the analogue ports of the ventilator and carry signals related to the pressure and flow respectively. The connection 19 is to the digital port of the ventilator 16 and provides an RS-232 link to the computer 15.

Figure 4:
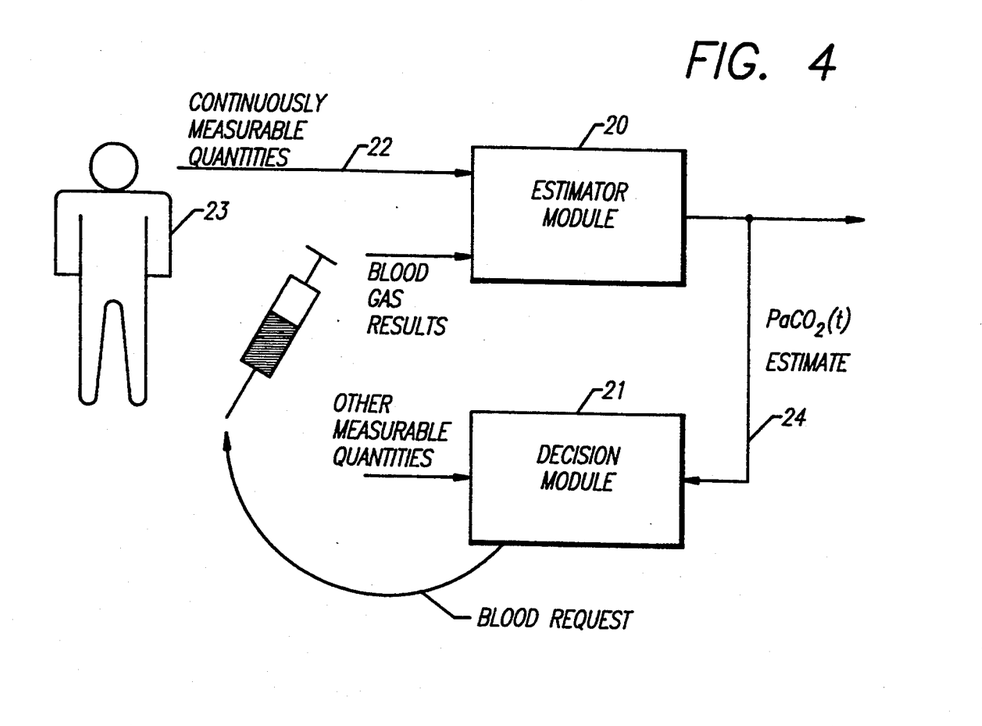
FIG. 4 is a schematic diagram showing the main method steps according to the invention.

Referring now to FIG. 4, the method in fact involves two major modules, the first of which is the $PaCO_2$ estimator 20 and the second of which is the decision module 21. The estimation module 20 receives information on input 22 related to measurements taken from each breath of patient 23, that is, by a breath-by-breath analysis. The decision module 21 receives information on input 24 obtained from other measurable quantities relevant to the patient such as lung mechanics and trends in $CO_2$ production for example, and contains decision rules obtained by previous experimentation. The rules are implemented as the rule-base of an Expert system.

The $PaCO_2$ estimator 20 is described by equation (1).

$$\frac{V_D^{alv}}{V_T^{alv}} = \frac{PaCO_2 - \overline{PE}^*CO_2}{PaCO_2 - PiCO_2} \quad (1)$$

where $V_D^{alv}$ is the alveolar deadspace,
$V_T^{alv}$ is the alveolar tidal volume,
$\overline{PE}.CO_2$ is the mixed-expired $CO_2$ from the alveolar tidal volume, and
$PiCO_2$ is inspired $CO_2$.

The deadspace ratio is the ratio of alveolar deadspace to alveolar tidal volume.

Figure 3:
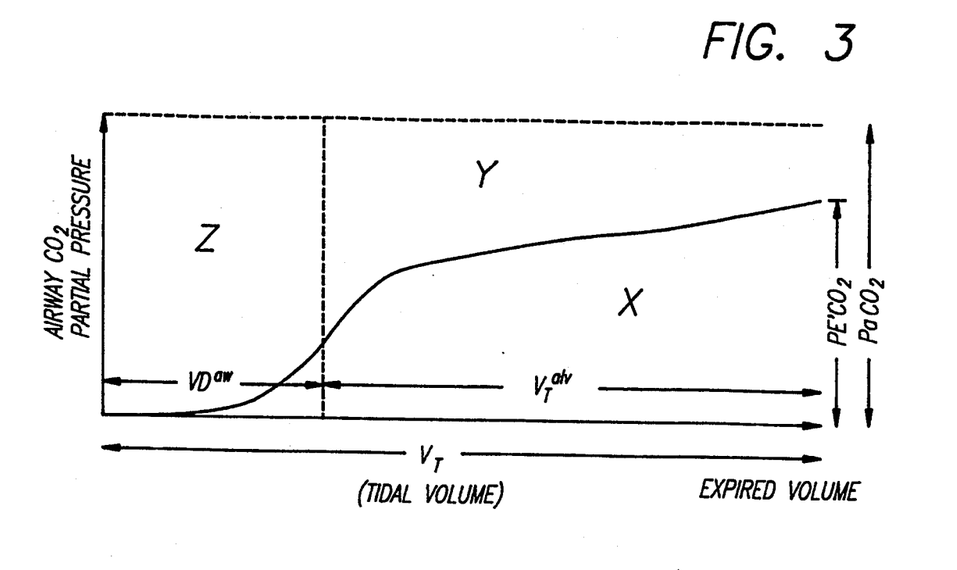
FIG. 3 is a graph of airwave $CO_2$ partial pressure versus expired volume for each breath of the patient.

The various parameters may be obtained from the plot of airwave $CO_2$ partial pressure versus expired volume for each breath a shown in the single breath test graph of FIG. 3 On the graph $PE^1CO_2$ is end tidal $CO_2$, and $V_T^{alv}$ is tidal volume involved in gas exchange. The alveolar deadspace (represented by area Y) is that part of inspired gas which reaches the alveoli but does not take part in gas exchange. $VD^{aw}$, the airway deadspace, is the point of maximum inflection of the plot. From FIG. 1, $PE.CO_2$ and $PiCO_2$ may be found using Equation (2)-(5).

$$\overline{PE}^*CO2 = \text{area}X/V_T^{alv} \quad (2)$$

$$PiCO_2 = \overline{PE}^*CO_2 - \overline{PE}^{*bag}CO_2 \quad (3)$$

$$\overline{PE}^{bag}CO_2 = \overline{PE}^{bag}CO_2 * V_T/V_t^{alv} \quad (4)$$

$$\overline{PE}^{bag}CO_2 = \frac{\dot{V}CO_2 * 863}{V_T * f} \quad (5)$$

where f is the respiratory rate. $\dot{V}CO_2$ is carbon dioxide production which can be calculated each minute by integrating the $CO_2$ fraction ($FCO_2$) and the flow signal, as shown in Equation (6)-(7).

$$\dot{V}CO_2 = \sum_{k=1}^{1 \text{ min}} \dot{V} * FCO_2 \quad (6)$$

$$FCO_2 = \frac{PCO_2}{P_{airway} + P_B + P_{H2O}} \quad (7)$$

where $\dot{V}$ is flow, $FCO_2$ is fraction of $CO_2$, $PCO_2$ is the capnograph signal, $P_{airway}$ is airway pressure, $P_B$ is barometric pressure and $P_{H2O}$ is vapor pressure.

Breath-by-breath processing yields the mixed expired $CO_2$, inspired $CO_2$, alveolar tidal volume and the airway deadspace. The only unknowns being $PaCO_2$ obtained after a blood sample analysis, the deadspace ratio can be calculated. Assuming that the deadspace ratio remains subsequently constant, further $PaCO_2$ can be calculated using Equation (1). A $PaCO_2$ estimate is calculated once every minute based on the average of the breaths in the minute.

Certain corrections are needed when implementing the system as set forth below:

(a) Flow signals have to be corrected form BTPS (Body Temperature Pressure Saturated) to STPD (Standard Temperature Pressure Dry).

(b) Correction must be made for delay-time between the flow signals and capnograph signals. Delay time is found by simple breath-holding and rapid expiration through the airway tubing, and lining up the start of flow and capnograph signals.

(c) Correction for compliance of the airway tubing. Flow due to compliance volume is subtracted form the analog flow signal, using $$\frac{dP}{dt} C = V,$$

where P=airway pressure,
C=tubing compliance,
V=flow due to compliance.

(d) Correction for rebreathing is done by continuously integrating flow and $CO_2$ fraction, using Equation (6).

(e) Correction of capnograph signal for vapor pressure and airway pressure is done by Equation (7).

As mentioned above the decision rules are obtained by experimentations to determine rules which indicate a change in the deadspace ratio whereby the system may signal that a new blood test is required.

The following are the decision rules derived:

(i) If Alveolar minute volume increases and $CO_2$ production decreases, deadspace ratio may have changed.

(ii) If Alveolar minute decreases and $CO_2$ production increases, deadspace ratio may have changed.

(iii) If Alveolar minute volume increases and arterial or end-tidal $CO_2$ increases, deadspace may have changed.

(iv) If Alveolar minute volume decreases and arterial or end-tidal $CO_2$ decreases, deadspace may have changed.

It is possible to derive further rules to indicate a change in deadspace ratio. For example, changes to airway resistance, peak airway pressure (PAP), peak flow, $SaO_2$, inspiratory to expiratory ratio, and positive end-expiratory pressure (PEEP) should indicate a change in the deadspace ratio. By automatically recording these parameters during a clinical trial, including blood test results, correlation between the change in parameters and change in deadspace ratio can be performed.

If desired, a closed-loop control of ventilation may be implemented based on the predicated PaCO$_2$. The controller in this case is a set of rules which decides on the tidal volume and respiratory rate settings for the mechanical ventilator, to achieve and maintain PaCO$_2$ at a set-point. The controller rules are based on existing clinical protocol for ventilator settings.

The control algorithm is presented below:

First, a PaCO$_2$ setpoint has to be determined as follows:

Given the pH value from the most recent blood gas result, if pH is between 7.36 and 7.44, the PaCO$_2$ setpoint is 40 mm Hg, the default value. If pH exceeded the limits, the following equation is used to calculate a new PaCO$_2$ setpoint.

$$pH = 6.1 + \log(HCO_3/(0.03 * PaCO_2))$$

where pH=7.4, and HCO$_3^-$ is from the most recent blood gas analysis results. The PaCO$_2$ setpoint can also be set by the clinician, overriding the above calculations.

Next, ventilation settings for the next 5 minutes can be set by the following equation.

$$PCO_2, (V_T^{alv} * f) = PaCO_2' * (V_T^{alv} * f')$$

where PaCO$_2$ is the setpoint ($V_T^{alv} * f$) is the alveolar minute ventilation needed to achieve the setpoint, PaCO$_2'$ is the latest estimation and ($V_T^{alv} * f'$) is the latest minute ventilation.

To decide on the actual V$_T$ and f, from the minute volume, the following procedures are followed:

Increase V$_T$ and keep f constant, so that (1) V$_T$ is not smaller then 500 ml.
(2) V$_T$ is not bigger than 1000 ml.
(3) Peak airway pressure (PAP) is not greater than 40.

If (2) or (3) cannot be satisfied, keep V$_T$ constant and increase f such that (a) f is not smaller than 10 bpm.
(b) f is not bigger than 20 bpm. (and not less than 10 bpm.)
(c) Inspiratory to expiratory ratio (I:E) is smaller than 1:2.

If (b) or (c) is exceeded, Peak air flow (PAF) should be increased.

If the required minute volume cannot be achieved without exceeding the limits in any one of VT/f/PAP/-mean pressure/PAF/I:E, a warning message will be displayed to alert the clinician.

As is evident above, the system of the invention is implemented, according to one embodiment, on a PC-AT computer. Analogue flow and pressure signals from the Puritan-Bennett 7200 ventilator and airwave CO$_2$ signals from the HP-78356 capnograph are analogue-to-digital converted and processed in real time using the computer. Each breath is checked to reject unphysiological waveforms, such as incomplete spontaneous breaths, before further processing. A PaCO$_2$ estimate is calculated every minute and the decision rules are invoked.

Tests have been performed to verify all calculations made in formulating the decision rules. CO$_2$ production and mixed-expired CO$_2$ were tested against the Douglas bag method. Air way deadspace was checked by introducing a known deadspace into the ventilator circuit. Corrections had to be made to account for airway tubing compliance, time delay between the flow and capnograph signal, and rebreathing. To test the accuracy of PaCO$_2$ estimation, clinical trials were carried out on ICU patients. For each patient, tidal volume and ventilation rate were changed in different combinations to a maximum of 30% of the initial settings. After each change and a stabilization period of about 10 minutes, a blood sample was drawn to check the estimation. Each clinical experiment involved 6–8 manipulations, over 90 minutes.

To identify the factors and the degree that they affect the alveolar deadspace ratio, specific procedures are incorporated into the clinical experiments to change the deadspace. Posture of the patient is changed by tuning the patient or inclining of the bed. Another procedure has been to administer bronchodilators. Various measurable parameters are recorded during the experiments for correlation with deadspace changes. These include airway compliance and resistance, peak airway pressure, peak air flow, inspiratory time, positive end-expiratory pressure (PEEP), inspiratory to expiratory ratio (I:E), slope of the CO$_2$ versus expired-volume waveform, end-tidal CO$_2$ and SaO$_2$.

The test results show reliable estimation ($\pm 5$ mmHg) of PaCO$_2$, even when deadspace ratio changed by up to 30% of the initial value. This indicates that the estimator is robust to some changes in the deadspace ratio.

Figure 5:
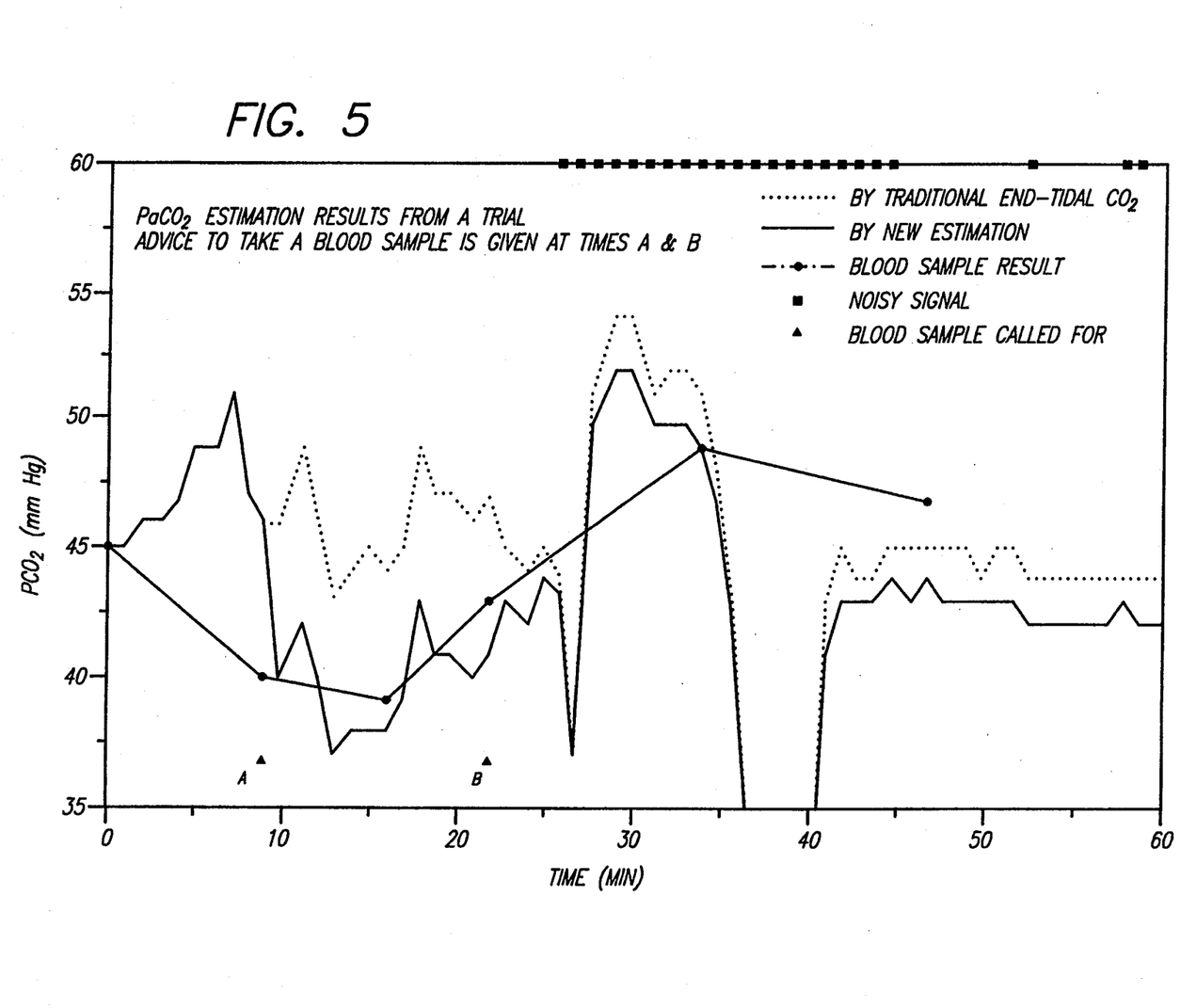
FIG. 5 is a graph of test results showing $PaCO_2$ estimation.

Test results also showed that deadspace ratio change can be expected when alveolar tidal volume and frequency changes are not followed by expected changes in end-tidal CO$_2$, estimated PaCO$_2$ or CO$_2$ production. Results from a trial are presented in FIG. 5. At point A, the increase in alveolar tidal volume and ventilation rate product (alveolar minute-volume) is not followed by a drop in both end-tidal CO$_2$ and estimated PaCO$_2$, indicating a blood test is needed. At point B, alveolar minute-volume decrease is not followed by an increase in end-tidal CO$_2$. In each case, the new estimation system correctly identifies the deadspace ratio change and estimates PaCO$_2$ reliably, compared to using the traditional method based on a constant arterial—end tidal difference.

Changes to compliance and resistance, peak airway pressure, peak flow, SaO$_2$ and I:E should indicate a change in the deadspace ratio but more results are needed before these relationships can be quantified.

The results show that the PaCO$_2$ estimator is sufficiently robust to permit continuous estimation for a wide range of ventilator settings. For large deadspace changes, the experimentally derived rules can be relied upon to signal for a blood gas test. Nevertheless, further clinical runs are necessary to cover all possible cases of deadspace ratio changes. By incorporating an Expert System, the knowledge base may be easily extended as more clinical data becomes available.

Figure 6A:
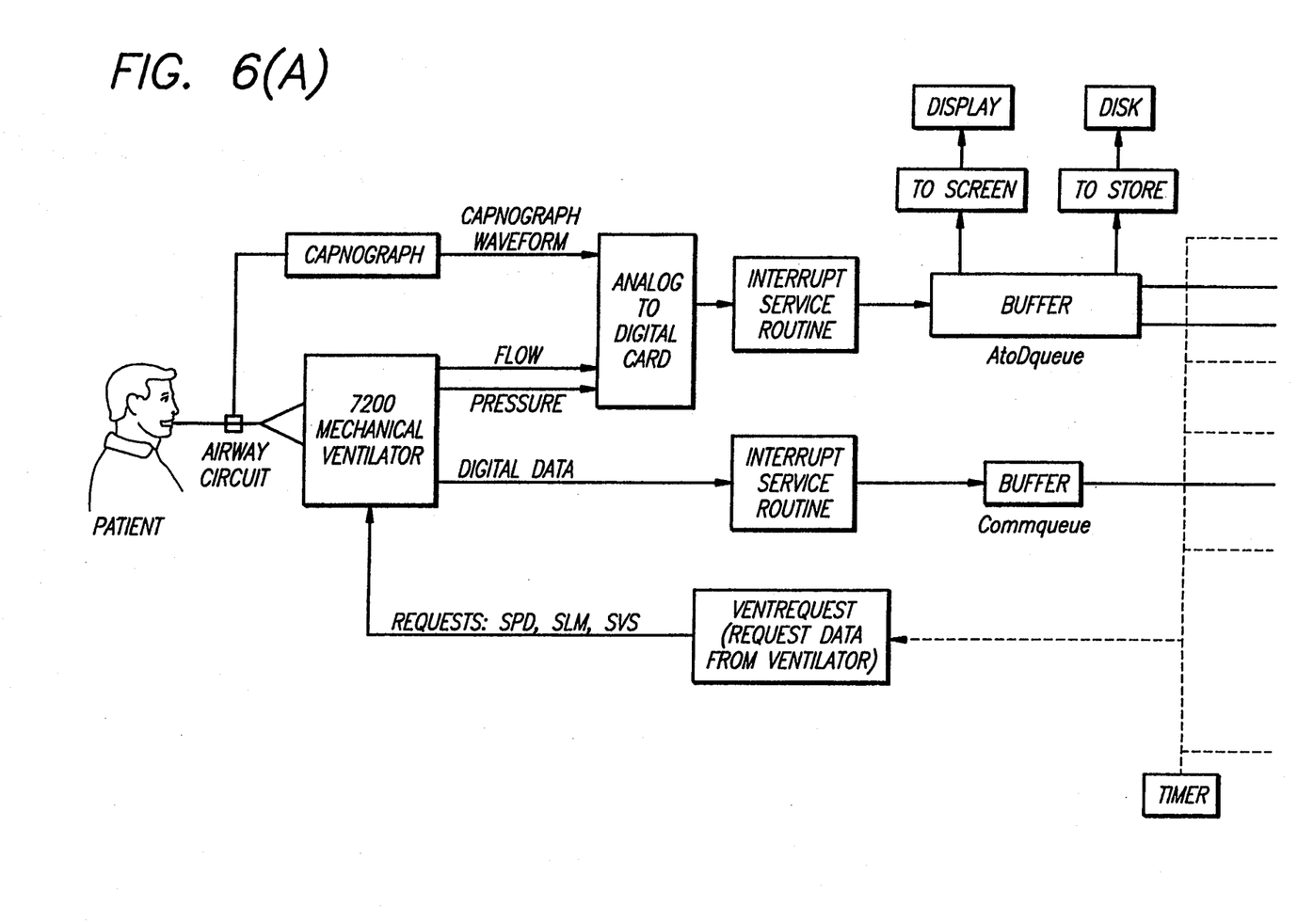
FIGS. 6(A) and 6(B) show a detailed functional block diagram of the apparatus of the invention.
Figure 6B:
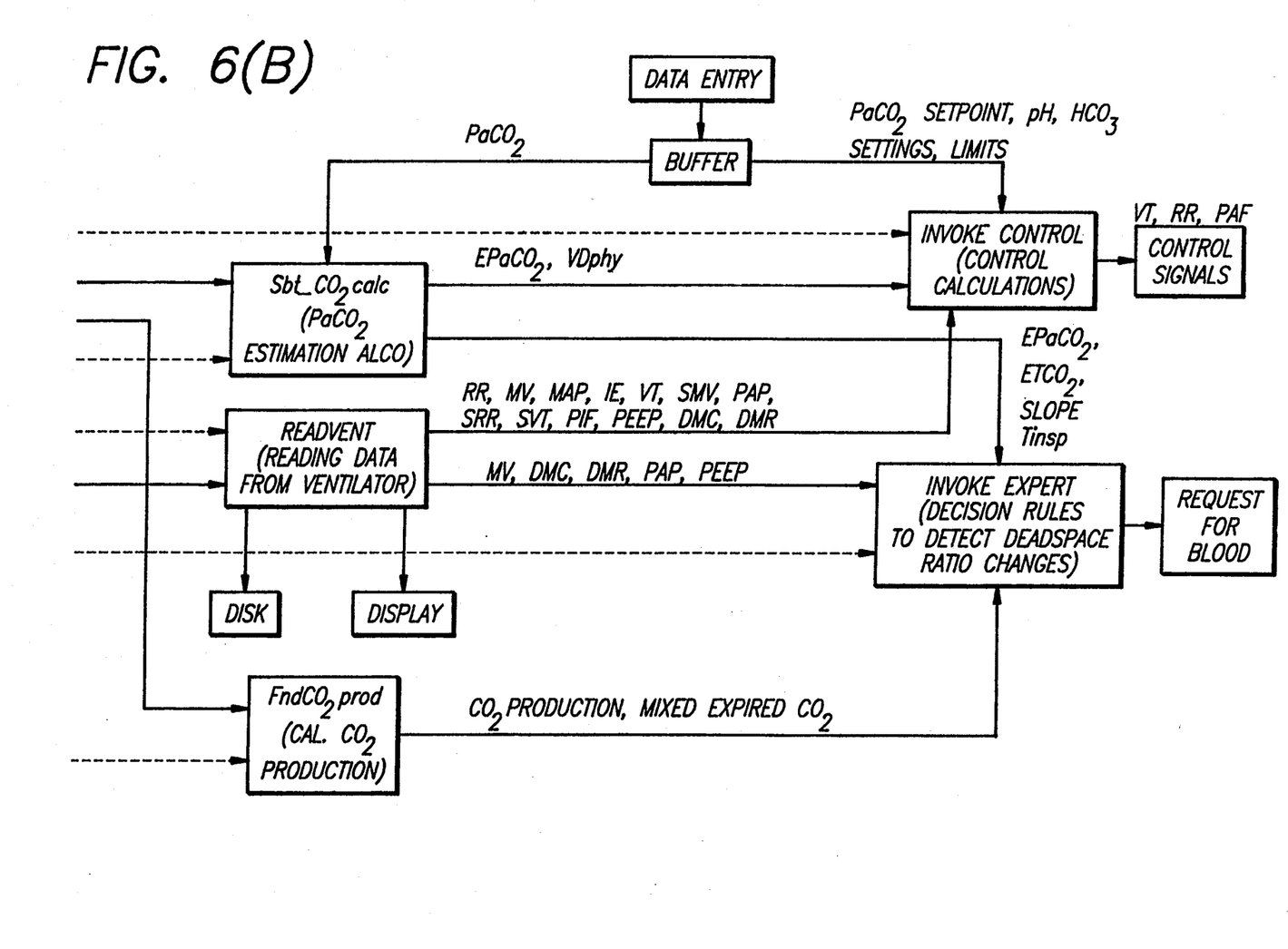

For the purpose of an even fuller understanding of the invention, the following description provides the pseudo code for programming the apparatus according to the invention. The program should be read in conjunction with FIG. 6 which is a self-explanatory functional block diagram of the apparatus.

MAIN PROGRAM

System setup: Hardware setup and parameters initialization.

Repeat

Timer: Keeping track of real-time, using each interrupt service form fixed-frequency AtoD conversion as time counter. Sets flags after each minute ("onemin"

flag) and five minutes ("fivemin" flag). If "one min" flag is true,
   Ventrequest: Request data from ventilator by sending request codes to serial port. The first request is "SPD" send patient data
   FndCO2prod: Request calculate carbon dioxide production and mixed expired carbon dioxide for the minute.
   Checkcomq: checking comm. queue. If queue is not empty,
   Readvent: Read characters received from ventilator.
   If calculation above are satisfactory,
      Sbt_CO2calc: Request calculation of physiological parameters and PaCO2 prediction.
   If "fivemin" flag is true and calc. above are satisfactory,
      InvokeExpert: Test if deadspace ratio changes.
      InvokeControl: Control rules.
   Checkkey: Check keyboard for keyhit. If Keyhit,
      Processkeyhit: "M" for marking of blood taken. Entering of PaCO2, pH, HCO3.
      "Q" to exit from program.
   If hardware test failed,
      Safe-exit.: Disables all interrupts, turn off A/D conversion, and close all files before exiting.
   If 0.5–4.0 seconds have elapsed, process data from queue:
      Toscrn: Display on screen.
      Tostore: Store in file.
      FndCO2prod: ongoing CO2 production calc.
      Sbt_CO2calc: Ongoing SBT calc.
   Until exit from system

SYSTEM SETUP

Initialize variables.
Initialize graphics (axes for plotting, etc.)
Hardware setup: Setting up interrupts for digital and analog interfacing.

HARDWARE SETUP

Setup a circular buffer (AtoDqueue) for storing real-time data.
Set up a circular buffer (Commqueue) for storing character strings received from serial port.
Program Analog to Digital Conversion card to convert at set frequency (100Hz), and to generate an interrupt on completion of each conversion, for the first channel of three. (The three channels are the airway flow, pressure and capnograph signals.)
Set and enable interrupt vector (Interrupt Service Routine: SetAtoD) for A/D card, to read analog flow and pressure from the ventilator, and capnograph waveform from the capnograph.
Set and enable interrupt vector (Interrupt Service Routine: SetComm) for serial port, to read digital data from ventilator.

INTERRUPT SERVICE ROUTINE: SetAtoD

Increment timing counter, for "Timer" routine.
Read converted data from port.
Request and read the other two channels. (The three channels are flow, pressure and capnograph waveform).
Put delay time between flow, pressure waveforms and the capnograph waveform to synchronize the signals.
Put data into the circular buffer (AtoDqueue).

INTERRUPT SERVICE ROUTE: SetComm

Put characters received in circular buffer (Commqueue).

TIMER

If "onemin" or "fivemin" flag has been set, clear it (Token removal to ensure that the token is passed around the real-time loop only once).
Checks timing counts. (Generated by ISR, SetAtoD).
If one minute has elapsed, set "onemin" flag.
If five minutes have elapsed, set "fivemin" flag.

FndCO2 prod

During ongoing calculations (by the data count),
   Repeat from queue head to tail,
      Read $CO_2$ (mmHg), airway flow. (Lpm) and pressure signals (mmHg).
      Calculate $CO_2$ fraction: $CO_2$ fraction = $CO_2/(PB - P_{H20} + \text{pressure})$, where PB=760, $P_{H20}=47$.
      Correction for flow:
         Flow(Lpm)=flow:
         Compliance * (pressure-previous pressure) * 60/PTTOMS, where
         Compliance=5.17 ml/mmHg, PTTOMS=10.
      If airway flow $> +1.2$ lpm (expiration phase),
         $CO_2$flow=CO, flow+flow*$CO_2$fraction.
      (Integration of airway flow and $CO_2$ fraction)
      Expvol=expvol+flow. (Calculation of expired volume in the breath)
   If request for a minute's $CO_2$ production,
      $CO_2$production=$CO_2$ flow * BTPStoSTPD * PTTOMS/60.
      where BTPStoSTPD=0.8262.
      Expvol (ml)=expvol * BTPStoSTPD * PTTOMS/60.
      Mixed-expired
      $CO_2$(mmHg)=$CO_2$ production,863*0.8262/Expvol.
   Return

READVENT

Read characters from circular buffer (Commqueue). If carriage return is encountered (ie. end of message received),
   Check whether the heading of message is SPD (send patient data), SLM (send lung mechanics) or SVS (send ventilator status).
   For each message received, error checking by size of message, and whether various parameters read are within physiological range.
   If SPD is received, SLM will be requested.
   If SLM is received, SVS will be requested.
   If SVS is received, and if all data are acceptable, a flag will be set to indicate completion of ventilator requests.
(Parameters read from ventilator include: RR (rate), MV (minute volume), MAP (mean air pressure), IE (inspiratory to expiratory ratio), VT (tidal vol), SMV (spontaneous MV), PAP (peak airway pressure), SRR (set rate), SVT (set VT), PIF (peak inspiratory pressure), PEEP (positive end expiratory pressure), DMC (Dynamic Compliance), DMR (Dynamic Resistance)).

Sbt CO2calc

If ongoing calculation,
   For each breath, if flow $< -1.2$Lpm (inspiration phase), Tinsp (inspiratory time) is counted.
For each breath, if flow $> +1.2$Lpm (expiration),
  Correct for compliance flow.
  Calculate tidal volume(Vt):
    Expvol(ml)=expvol+(flow*PTTOMS/1000).
  Plot Single Breath $CO_2$ Expiration curve (airway $CO_2$ (mmHg) vs expvol(ml)).
  Calculate gradient of airway $CO_2$ vs expvol.
  Record the maximum inflection point of $CO_2$ vs expvol;
  This is the airway deadspace, $VD_{airway}$.
At end of expiration (flow$< -1.2$Lpm),
  Reject data from the breath if waveform is unphysiological (Less than 50 data points, or maximum inflexion point is not found).
  Determine end-tidal $CO_2$, the maximum airway $CO_2$.
  Calculate the plateau slope of $CO_2$ vs expvol.
  Calculate the area under the Single Breath $CO_2$ (area X), by summation.
  Parameters calculated for this breath are summed with parameters from previous breaths within a minute. The parameters are: the number of breaths, areaX, $VD_{airway}$, tidal volume ($V_T$), end-tidal $CO_2$ (ETCO2), plateau phase slope, Tinsp and number of rejected waveforms.
If request for a $CO_2$ prediction,
  If arterial $CO_2$ sample is drawn (marked) but not available yet,
    The minute's parameters are kept in a buffer.
  If arterial $CO_2$ is available,
    An average for all parameters over the last minute is calculated. (The average value of each parameter is the summation/total number of breaths.)
    From the average, the following calculations are done:
    $V_T^{alv}$ (alveolar tidal vol)=$V_T - VD_{airway}$.
    PE*CO2 (bag mixed expired $CO_2$)=area X/$V_T^{alv}$.
    $PE^{bag}CO_2$ (bag mixed expired $CO_2$)=
    CO2prod,863/($V_T$*f)
    $PE^{bag}CO_2 = PE^{bag}CO_2 * V_T/V_T^{alv}$.
    $PiCO_2 - PECO_2 = PE^{bag}CO_2$.
    If PaCO2 is new,
      Calculate new deadspace ratio: $V_D^{alv}$(alveolar deadspace)=$VT^{alv}$ (PaCO2)/(PaCO2-PiCO2).
      Alvcon (deadspace ratio)=$V_D^{alv}/V_T^{alv}$.
      VDphy(physiological deadspace)=$V_D^{alv}/AD_T^{airway}$.
    Estimated PCO2 (EPaCO2)=(PECO2-Alvcon-PiCO2)/(1-Alvcon).
InvokeExpert: Rules to check if deadspace ratio has changed.
(Parameters needed are: MV, ETCO2, EPaCO2, CO2prod, slope, DMC, DMR, Tinsp, PEEP, PAP).
Whenever the rules below are triggered three times consecutively, a warning is generated (Note that the parameters are compared with the values obtained from the most recent blood gas results):
If MV increases by 800 ml or more and ETCO2 does not drop by at least 2 mmHg.
If MV decreases by 800 ml or more and ETCO2 does not increase by at least 2 mmHg.
If MV increases by 800 ml or more and EPaCO2 does not drop by at least 2 mmHg.
If MV decreases by 800 ml or more and EPaCO2 does not increase by at least 2 mmHg.
If MV increases by 800 ml or more and CO2prod does not increase by at least 20 ml.
If MV decreases by 800 ml or more and CO2prod does not decrease by at least 20 ml.
If slope changes by more than 0.5 mmHg/ml.
IF DMR changes by more than 10 cmH2O/L/s.
IF DMC changes by more than 10 ml/cmH2O.
If Tinsp changes by more than 0.5 s.
If PAP changes by more than 10 cmH2O.
If previous PEEP is less than 10 cmH2O and changes by more than 5 cmH2O.
If previous PEEP is equal or more than 10 cmH2O and changes by more than 2 cmH2O.
InvokeControl: Rules for ventilator control. (Parameters needed are:
  Entered from blood gas results: pH, HCO3, settings limits (I:E ratio minimum, rate limits, volume limits, peak pressure limit).
  From ventilator requests: RR, MV, MAP, IE, VT, SMV, PAP, SRR, SVT, PIF, PEEP, DMC, DMR.
  From Calculations: Vdphy, EPaCO2.)
  If new blood test result is available, calculate new $CO_2$ setpoint:
    If (pH$<7.36$) or (pH$>7.44$)
      $CO_2$ setpoint=1.6706,HCO3
  Calculate alveolar minute volume needed (AMVneeded);
    AMV (Alveolar minute volume(ml))=(MV,1000-RR*VDphy).
    AMVneeded=EPaCO2, AMV/CO2 setpoint.
  Correct for spontaneous breathing; If ( SMV$>0$) and (RR$>$SRR)
    RRspont (Spontaneous rate)=SRR-RR.
    AMVneeded=AMVneeded—(SMV, 1000-RRspont,VDphy).
  Control.

Control

Calculate an initial tidal volume needed using current frequency, to produce the required minute volume:
newVT=(AMVneeded/RR)+VDphy.
If PAP$>$PAP limit,
  Repeat
    Check the proposed VT & RR to rest if their limits have been exceeded (CheckVT, CheckRR);
    Results of these checks are entered into the look-up table. Calculate VT & RR using look-up table 1; Results from look-up table decides whether calculated settings are acceptable.
  Until the result from look-up table is either "Implement" or "Impossible".
else
Repeat
  Check VT & RR if limits exceeded.
  Calculate VT & RR using look-up table 2.
Until the result is either "Implement" or "Impossible".

Checking VT & RR

CheckVT:

If VT$>$maximumVT, result is "Not Increase".
If VT$<$minimumVT, result is "Not Decrease". Otherwise result is "OK".

Check RR:

If RR$>$maximumRR, result is "Not Increase RR".
If RR$<$minimumRR, result is "Not Decrease RR".
Otherwise result is "OK".

Lookup tables

After doing the checks for VT & RR, the VT & RR results are used with the appropriate look-up table to determine the next calculation.

Lookup Table 1

| RR result | VT result | | |
|---|---|---|---|
| | OK | Not Increase | Not Decrease |
| OK | Implement | Drop V | Inc V |
| Not increase | DropRR | Impossible | Inc V |
| Not Decrease | Inc RR | Drop V | Impossible |

Lookup Table 2

| RR result | VT result | | |
|---|---|---|---|
| | OK | Not increase | Not Decrease |
| OK | Implement | Drop V | Impossible |
| Not Increase | Impossible | Impossible | Impossible |
| Not Decrease | Drop V | Drop V | Impossible |

If result is "Inc V" increase VT by 50 ml
If result is "Drop V", decrease VT by 50 ml.
If VT has changed, calculate new RR for the required minute volume (AMVneeded):
  new RR=AMVneeded/(VT−VDphy).
If result is "Inc RR" increase RR by 1 BPM
If result is "Drop RR" decrease RR by 1 BPM
If RR has changed, calculate new VT for the required AMVneeded:
  new VT=(AMVneeded/RR)+VDphy.
If result from the look-up tables is "Implement",
  If (IE<minimumIE)
  If (new RR is bigger or equal to the current setting)
  Increase PAF by 10 LPM. (Ensure IE ratio is above the minimum by increasing peak air flow).
  Implement the new VT & RR.
If result is "Impossible",
  A warning alarm is generated to indicate inability to implement required settings.

It will be apparent from the foregoing that while particular forms of the invention have been illustrated and described, various modifications can be made without departing from the spirit and scope of the invention. Accordingly, it is not intended that the invention be limited, except as by the appended claims.

We claim:

1. A method of continuously and non-invasively monitoring arterial blood $CO_2$ partial pressure of artificially ventilated patients by monitoring a patient's breath, and determining $PaCO_2$ based upon a determination of a deadspace ratio, comprising the steps of:
   a) continuously monitoring measurable parameters of a patient's breath;
   b) measuring the $PaCO_2$ from a blood sample of the patient and obtaining an input value; calculating the deadspace ratio using the patient's breath parameters and said input value; and
   c) continuously determining $PaCO_2$ based on an assumption that the deadspace ratio subsequently remains constant.

2. The method of claim 1, wherein said step of continuously monitoring measurable parameters of a patient's breath comprises monitoring mixed-expired CO2 partial pressure, inspired CO2 partial pressure, and alveolar tidal volume.

3. The method of claim 2, wherein said step of continuously monitoring measurable parameters of a patient's breath further comprises monitoring alveolar deadspace.

4. The method of claim 1, wherein said step of continuously determining $PaCO_2$ is based upon the equation $$V_D^{ALV}/V_T^{ALV} = (PaCO_2 - PE^*CO_2)/(PaCO_2 - PiCO_2)$$

where $V_D^{ALV}$ is alveolar deadspace,
$V_T^{ALV}$ is alveolar tidal volume,
$PE^*CO_2$ is mixed-expired $CO_2$ partial pressure from the
alveolar tidal volume, and
$PiCO_2$ is inspired $CO_2$ partial pressure.

5. The method of claim 1, further comprising the steps of identifying an onset of changes in the deadspace ratio by decision rules obtained from other measurable data; and determining a new deadspace ratio from the patient's breath parameters and a further input value of PaCO2 from the patient's blood sample.

6. The method of claim 5, wherein said step of identifying an onset of changes in the deadspace ratio by decision rules obtained from other measurable data comprises monitoring parameters related to lung mechanics and changes in CO2 production as measured by PE.CO2 partial pressure from the alveolar tidal volume.

7. The method of claim 1, further comprising the step of adjusting patient ventilation based on the determined value of $PaCO_2$.

8. An apparatus for continuously and non-invasively monitoring arterial blood CO2 partial pressure of artificially ventilated patients, comprising:
   a) means for monitoring continuously measurable parameters relevant to a patient's breath and providing data relating thereto;
   b) means for obtaining an input value corresponding to the $PaCO_2$ of a blood sample from the patient; means for determining a deadspace ratio, connected to receive said input value and the patient's breath parameter data, wherein said means for determining calculates the deadspace ratio from the input value and the patient's breath parameter data; and
   c) means for continuously determining PaCO2 based on the deadspace ratio, and an assumption that the deadspace ratio remains subsequently constant.

9. The apparatus of claim 8, wherein said means for monitoring continuously measurable parameters relevant to a patient's breath and providing data relating thereto comprises a capnograph.

10. The apparatus of claim 8, wherein said means for determining a deadspace ratio comprises a microprocessor.

11. The apparatus of claim 8, further including means for identifying an onset of changes in the deadspace ratio to thereby signal a need for a further blood sample to re-calculate the deadspace ratio, based upon decision rules.

12. The apparatus of claim 8, further including means for controlling the operation of a mechanical ventilator based upon the values of PaCO2 determined by the apparatus.

* * * * *

UNITED STATES PATENT AND TRADEMARK OFFICE
CERTIFICATE OF CORRECTION

PATENT NO. : 5,402,796
DATED : Apr. 4, 1995
INVENTOR(S) : John S. Packer, John F. Cade, Eng-Boon L. Law It is certified that error appears in the above-indentified patent and that said Letters Patent is hereby corrected as shown below:

Column 1, line 49, after "monitoring" remove ",".
Column 2, line 3, change "$\overline{PE}.CO_2$" to --$\overline{PE}^*CO_2$--.
Column 3, line 35, change "$\overline{PE}.CO_2$" to --$\overline{PE}^*CO_2$--.
Column 3, line 49, change "$\overline{PE}.CO_2$" to --$\overline{PE}^*CO_2$--.

Column 5, line 25, change "$PCO_2$," to --$PCO_2^*$--.

Column 6, line 28, after "changes are not" delete the colon ":".
Column 6, line 40, change "arterial___end" to --arterial-end--.
Column 8, line 1, change "Route" to --ROUTINE--.
Column 8, line 28, change "$CO_2 flow=CO,$" to --$CO_2 flow=CO_2$--.
Column 8, line 39, change "production,863*" to --production*863*--.
Column 9, line 42, change $CO_2 Prod,863$" to --$CO_2 Prod*863$--.
Column 9, line 49, change "$=V_D^{alv}/AD_T^{air}$" to $=V_D^{alv} + A_D^{airway}$ --;
Column 10, line 25, change "$=1.6706,HCO_3$" to --$=1.6706*HCO_3$--.
Column 10, line 28, change "(MV,1000-" to --(MV*1000- --.
Column 10, line 34 & 35, change "(SMV, 1000- $RR_{spont}, VD_{pby})$" (SMV*1000-$RR_{spont}*VD_{phy}$) --.
to-- (SMV*1000 - RRspont*VDphy) --.

Page 1 of 2

UNITED STATES PATENT AND TRADEMARK OFFICE
CERTIFICATE OF CORRECTION

PATENT NO. : 5,402,796
DATED : Apr. 4, 1995
INVENTOR(S) : John S. Packer, et al.

It is certified that error appears in the above-indentified patent and that said Letters Patent is hereby corrected as shown below:

Claim 6, column 12, line 30, change "$PE,CO_2$" to --$PE*CO_2$--.

Signed and Sealed this

Eighteenth Day of June, 1996

BRUCE LEHMAN

Attest:

Attesting Officer    Commissioner of Patents and Trademarks